United States Patent [19]

Reuvers et al.

[11] Patent Number: 4,645,855
[45] Date of Patent: Feb. 24, 1987

[54] PREPARATION OF SUCCINIC ACID DIESTERS

[75] Inventors: Johannes G. Reuvers, Viernheim; Wolfgang Richter, Ludwigshafen; Rudolf Kummer, Frankenthal, all of Fed. Rep. of Germany

[73] Assignee: BASF Aktiengesellschaft, Ludwigshafen, Fed. Rep. of Germany

[21] Appl. No.: 644,496

[22] Filed: Aug. 24, 1984

[30] Foreign Application Priority Data

Sep. 6, 1983 [DE] Fed. Rep. of Germany ....... 3332018

[51] Int. Cl.[4] .............................................. C07C 67/03
[52] U.S. Cl. .................................... 560/204; 502/152; 502/326; 560/193; 568/852; 568/853; 568/858
[58] Field of Search ................ 560/193, 204; 568/853, 568/858, 852

[56] References Cited

U.S. PATENT DOCUMENTS 3,830,830  8/1974  Cleveland et al. ................. 560/204
4,258,203  3/1981  Platz et al. ........................... 560/204
4,404,394  9/1983  Isogai et al. ......................... 560/204

OTHER PUBLICATIONS

A. Matsuda, *Bull. Chem. Soc.* Japan, vol. 42, (1969), 571–72.

*Primary Examiner*—Natalie Trousof
*Assistant Examiner*—Vera C. Clarke
*Attorney, Agent, or Firm*—John H. Shurtleff

[57] ABSTRACT

A process for the preparation of succinic acid diesters by carbonylation of acrylic acid esters in the presence of alcohols, using a cobalt carbonyl complex as the catalyst and a heterocyclic nitrogen base as the promoter, at 80°–200° C. and under a carbon monoxide pressure of 60–300 bar, wherein the reaction is carried out in the presence of not less than 20% by weight, based on the amount of all the liquid constituents of the reaction mixture, of an inert liquid and the concentration of the acrylic acid ester is kept, for the predominant part of the reaction time, at below 15% by weight, again based on the amount of all liquid constituents.

8 Claims, No Drawings

PREPARATION OF SUCCINIC ACID DIESTERS

The present invention relates to an improved process for the preparation of succinic acid diesters by carbonylation of acrylic acid esters in the presence of alcohols, using a cobalt carbonyl complex as the catalyst and a heterocyclic nitrogen base as the promoter, at 80°–200° C. and under a carbon monoxide pressure of 60–300 bar.

The carbonylation of olefinically unsaturated compounds under the above conditions forms the subject of numerous researches and is accordingly generally known.

In particular, it is known from A. Matsuda in Bull. Chem. Soc. Japan, 42 (1969), 571–72, that methyl acrylate and methanol may in this way be converted to dimethyl succinate:

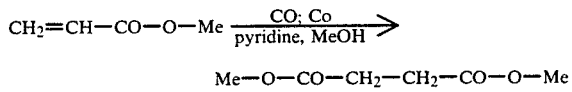

$$CH_2=CH-CO-O-Me \xrightarrow[\text{pyridine, MeOH}]{CO; Co}$$

$$Me-O-CO-CH_2-CH_2-CO-O-Me$$

It is true that the methyl acrylate undergoes complete conversion, but the yields of dimethyl succinate are not more than 82%. The remainder is very largely attributable to byproducts, not investigated in more detail, with minor proportions of the dimethyl esters of methylmalonic acid (the isomeric carbonylation product of the acrylic ester) and of 3-ketopimelic acid.

Since in this process virtually one fifth of the methyl acrylate employed is thus lost, the process cannot be considered for industrial purposes.

It is an object of the present invention so to design the carbonylation of acrylic acid esters with carbon monoxide and alcohols that succinic acid diesters are obtained in a simple manner and in satisfactory yields.

We have found that this object is achieved by an improved process for the preparation of succinic acid diesters by carbonylation of acrylic acid esters in the presence of alcohols, using a cobalt carbonyl complex as the catalyst and a heterocyclic nitrogen base as the promoter, at 80–200° C. and under a carbon monoxide pressure of 60–300 bar, wherein the reaction is carried out in the presence of not less than 20% by weight, based on the amount of all the liquid constituents of the reaction mixture, of an inert liquid and the concentration of the acrylic acid ester is kept, for the predominant part of the reaction time, at below 15% by weight, again based on the amount of all liquid constituents.

Inert liquids are to be understood, in the usual manner, at those which undergo no significant change, if any, under the reaction conditions. Inert liquids which form a homogeneous liquid phase with all other liquid constituents of the reaction mixture under the reaction conditions, so that the inert liquids serve as a solvent, are preferred. Since this is normally the case, the inert liquids are hereinafter referred to as solvents.

Suitable solvents of this type are in particular aromatic hydrocarbons, eg. benzene, toluene or the xylenes, as well as $C_6$–$C_{12}$-alkanes, eg. n-heptane and n-octane, and cycloalkanes, eg. cyclohexane. However, it is particularly advantageous to use, as the solvent, the succinic acid diester formed in the reaction.

From the point of view of the success of the process, there is no upper limit-according to our observations so far-to the concentration of the solvent. However, for technical and economic reasons a concentration range of 20–80, preferably 40–60, % by weight, is generally advisable.

According to the invention, the concentration of the acrylic acid ester employed must, over the predominant part of the reaction time, be kept at below 15% by weight based on the total amount of all liquid constituents. This means that endeavors must be made to observe this condition over the entire reaction time but that occasional exceeding of this concentration is not a significant disadvantage.

Preferably, the concentration of the acrylic acid ester is kept at below 5% by weight but, for technical and economic reasons, is not allowed to fall below 1% by weight.

Since the reaction is exothermic and the amount of heat liberated accordingly is a measure of the amount of acrylic acid ester converted, the feed rate of acrylic acid ester corresponding to maintenance of a particular concentration is readily determined. Another possible way of controlling the acrylic acid ester concentration is based on regular gas chromatography analyses of the reaction mixture. Once the feed rate of the acrylic acid ester has been determined in this or some similar manner, it no longer requires control of the concentration when running further reaction batches, or in continuous operation.

In other respects, the carbonylation is carried out in the conventional manner, namely at 80°–200° C., preferably 110°–170° C., and under a carbon monoxide pressure of 60–300 bar, preferably 120–280 bar.

The concentration of the cobalt catalyst is preferably between 0.01 and 10, especially between 0.1 and 2.0, % by weight of Co, based on the total amount of the liquid constituents of the reaction mixture (acrylic acid ester, alcohol, solvent, nitrogen base and process products).

The cobalt may be employed in the form of a readyprepared carbonyl complexes, eg. $Co_2(CO)_8$, or in the form of various cobalt compounds, eg. cobalt acetate, cobalt acetylacetonate or cobalt stearate, since the active cobalt complexes form of their own accord under the reaction conditions.

Amongst the promoters, pyridine deserves first mention, but alkylpyridines, such as the picolines, or isoquinolines, may also be used.

Preferably, not less than 2 moles of base are used per mole of cobalt, amounts of 10–40 moles being particularly recommended. Larger amounts, say up to 400 moles, can also be used but in general produce no further advantages.

The amount of alcohol should be not less than equimolar to the amount of acrylic acid ester but it is advisable to have the alcohol present in excess over the acrylic acid ester throughout the reaction; a molar ratio of 2–10 moles of alcohol per mole of acrylic acid ester is preferred.

The process according to the invention offers a very advantageous method of preparation but butane-1,4-diol by oxidizing propylene to acrylic acid, esterifying the latter to give an acrylic acid ester, carbonylating the ester together with an alcohol and hydrogenating the succinic acid diester in a manner known per se to give butane-diol and the alcohols.

Since the process is likely to prove of greatest industrial importance in respect of butanediol synthesis, the normal starting material will be the simplest and cheapest acrylic acid ester, namely methyl acrylate, and the simplest and cheapest alcohol, namely methanol.

On the other hand, the carbonylation process is not restricted to these and can in principle be employed successfully also for the reaction of other acrylic acid esters and other alcohols.

Accordingly, the alcohol component in the acrylic acid ester is generally an aliphatic, cycloaliphatic or araliphatic alcohol which is inert under the carbonylation conditions. $C_1$–$C_8$-alkanols, especially $C_1$–$C_3$-alkanols and amongst these, as already mentioned, particularly methanol, are preferred.

Similar remarks apply to the alcohols undergoing the carbonylation reaction.

If the alcohol radicals are intended to be cleaved again from the succinic acid diester, it is advantageous to employ the same alcohol for the carbonylation as that which is present in a chemically bonded form in the acrylic acid ester.

To prevent undesirable polymerization reactions it is advisable to carry out the carbonylation process according to the invention in the presence of effective amounts of polymerization inhibitors, such as hydroquinone or N,N'-di-β-naphthyl-p-phenylenediamine.

Using the process according to the invention, yields of succinic acid diesters of more than 90% are achievable, with virtually quantitative conversion.

EXAMPLE 1

258 g (3.0 moles) of methyl acrylate were added continuously over 3 hours to a mixture of 180 g (5.6 moles) of methanol, 15 g (0.44 mole) of dicobalt-octacarbonyl, 23.7 g (0.3 mole) of pyridine and 200 g of toluene (=about 50% by weight of the liquid constituents) at 130° C., under a CO pressure of 120–130 bar.

As found by gas chromatography analysis of samples taken at intervals of 30 minutes, the concentration of the acrylic acid ester, based on the liquid constituents of the reaction mixture, rose from 0.3 to 2.8% by weight.

After all the methyl acrylate has been added, the reaction mixture was kept for a further 3 hours at 130° C. under a CO pressure of 120–130 bar, to complete the conversion. Conventional working up of the reaction mixture by distillation gave dimethyl succinate in a yield of 94.2%.

Using the same amounts of the starting materials, the same temperature and the same pressure, but working in the presence of the total amount of methyl acrylate from the start (initial concentration about 39% by weight), the dimethyl succinate yield achieved was only 82.6%.

If the methyl acrylate was reacted gradually over 3 hours, but no solvent was used, the dimethyl succinate yield was only 76.5%.

On initially introducing the entire methyl acrylate and not using a solvent, but in other respects employing the same amounts of starting materials, the same temperature and the same pressure, the dimethyl succinate yield was only 75.5%.

EXAMPLE 2

Following the procedure according to the invention as described in Example 1, but at 150° C. and 280 bar, a dimethyl succinate yield of 95.1% was achieved. The concentration of methyl acrylate in this case rose from 0.3 to 2.5% by weight and dropped again to zero during the post-reaction.

Without using toluene and working with the total amount of methyl acrylate present from the start, the dimethyl succinate yield was only 81.0%.

EXAMPLE 3

Following the procedure according to the invention as described in Example 1, but with n-butyl acrylate as the acrylic ester and butan-1-ol as the alcohol, the dibutyl succinate yield was 91.2%.

EXAMPLE 4

Following the procedure according to the invention as described in Example 1, but with cyclohexyl acrylate as the acrylic ester and cyclohexanol as the alcohol, the dicyclohexyl acrylate yield was 90.0%.

EXAMPLE 5

Following the procedure according to the invention as described in Example 1, but with 270 g of dimethyl succinate as the solvent, the dimethyl succinate yield achieved was 94.5%, based on methyl acrylate converted.

We claim:

1. In a process for the preparation of succinic acid diesters by carbonylation of acrylic acid esters in the presence of alcohol, using a cobalt carbonyl complex as the catalyst and a heterocyclic nitrogen base as the promoter at 80°–200° C. and under a carbon monoxide pressure of 60–300 bar, the improvement which comprises:

carrying out the reaction in the presence of not less than 20% by weight, based on the amount of all the liquid constituents of the reaction mixture, of an inert liquid solvent selected from the group consisting of the succinic acid diester formed in the reaction, aromatic hydrocarbons, $C_6$-to-$C_{12}$ alkanes and cycloalkanes, and keeping the concentration of the acrylic acid ester, for the predominant part of the reaction time, at below 15% by weight, again based on the amount of all liquid constituents.

2. An improved process as claimed in claim 1 wherein the inert liquid solvent is selected from the group consisting of benzene, toluene, the xylenes, n-heptane, n-octane and cyclohexane.

3. An improved process as claimed in claim 1 wherein the inert liquid solvent is toluene.

4. An improved process as claimed in claim 1 wherein the concentration of the inert liquid solvent is 20–80% by weight.

5. An improved process as claimed in claim 1 wherein the concentration of the inert liquid solvent is 40–60% by weight.

6. An improved process as claimed in claim 1 wherein the concentration of the acrylic acid ester, for the predominant part of the reaction time, is kept below 5% by weight but not below 1% by weight, based on the amount of all liquid constituents.

7. An improved process as claimed in claim 1 wherein the acrylic acid ester is methyl acrylate and the alcohol is methanol.

8. An improved process as claimed in claim 1 wherein the inert liquid solvent is the succinic acid diester formed in the reaction.

* * * * *